(12) United States Patent
Zegelin et al.

(10) Patent No.: US 7,065,325 B2
(45) Date of Patent: Jun. 20, 2006

(54) SELF CALIBRATION OF SIGNAL STRENGTH LOCATION SYSTEM

(75) Inventors: Chris Zegelin, San Jose, CA (US); David P. Goren, Smithtown, NY (US)

(73) Assignee: Symbol Technologies, Inc., Holtsville, NY (US)

( * ) Notice: Subject to any disclaimer, the term of this patent is extended or adjusted under 35 U.S.C. 154(b) by 186 days.

(21) Appl. No.: 10/852,348

(22) Filed: May 24, 2004

(65) Prior Publication Data

US 2004/0266465 A1   Dec. 30, 2004

Related U.S. Application Data

(60) Provisional application No. 60/473,096, filed on May 23, 2003.

(51) Int. Cl.
*H04B 17/00* (2006.01)

(52) U.S. Cl. .................. 455/67.11; 455/67.14; 455/522; 455/69; 342/450; 342/458

(58) Field of Classification Search ............. 455/67.11, 455/67.14, 522, 69; 342/450, 458
See application file for complete search history.

(56) References Cited

U.S. PATENT DOCUMENTS

| | | | |
|---|---|---|---|
| 6,259,912 B1 * | 7/2001 | Si | 455/424 |
| 6,754,470 B1 * | 6/2004 | Hendrickson et al. | 455/67.11 |
| 6,947,734 B1 * | 9/2005 | Toubassi | 455/423 |
| 2003/0034851 A1 * | 2/2003 | Norman et al. | 331/66 |
| 2003/0146871 A1 * | 8/2003 | Karr et al. | 342/457 |
| 2004/0209574 A1 * | 10/2004 | Tsay et al. | 455/67.14 |

* cited by examiner

*Primary Examiner*—Danh Cong Le
(74) *Attorney, Agent, or Firm*—Baker Botts LLP

(57) ABSTRACT

A system for locating mobile units in a data communications system based on signal strength measurements of mobile unit transmissions is calibrated for variations in mobile unit transmitter power by determining range of a mobile unit from an access point using two way time ranging. The time ranging is compared to the value for range based on signal strength and a correction value for the mobile unit is updated based on the difference between range based on time ranging and the range based on signal strength.

6 Claims, 1 Drawing Sheet

SELF CALIBRATION OF SIGNAL STRENGTH LOCATION SYSTEM

PRIORITY CLAIM

This application claims the benefit of the filing date of provisional application Ser. No. 60/473,096, filed May 23, 2003 and assigned to the same assignee as the present invention.

BACKGROUND OF INVENTION

This invention relates to object location systems, and particularly to systems having a plurality of access points wherein mobile units communicate with the access points using a wireless data communications protocol, such as IEEE Standard 802.11. The invention particularly relates to systems wherein location of a mobile unit is determined by measuring the signal strength of mobile unit transmissions which are received by access points to estimate the range of a mobile unit from the access point. As used in this application the term "access point" is intended to apply to access points as contemplated by Standard 802.11, or other standards, that interface a computer or a wired network to the wireless medium, and also RF Ports and cell controllers connected thereto, as described in co-pending application Ser. No. 09/528,697, filed Mar. 17, 2000, the specification of which is incorporated herein by reference.

A major variable in determination of range of a mobile unit from an access point is the signal strength of the mobile unit. There can be significant variation in transmitted signal strength of transmitter cards (NIC cards) from different manufacturers and even in cards from the same manufacturer from different production runs. Further the transmitter signal strength may vary over the life of a mobile unit and the life of its rechargeable battery.

Differences in transmitter power for mobile units in a system can be calibrated out by doing a measurement of signal strength as received from a known distance and providing a correction factor that is identified with that particular mobile unit. Such calibration requires special calibration procedures for each mobile unit as it is put into service, and, unless units are recalibrated, cannot account for changes in transmitter power as the mobile unit or its battery ages.

It is therefore an object of the present invention to provide new and improved methods of measuring the transmission power of mobile units on a periodic basis to update the correction value associated with such units in a signal strength location system.

SUMMARY OF THE INVENTION

In accordance with the invention there is provided a method for calibrating an object location system wherein transmitting mobile units are located by measuring received signal strength of signals transmitted by the mobile units and received by access points distributed over an area. Data messages are sent from at least one of the access points to a mobile unit to be calibrated. Acknowledgement signals from the mobile unit in response to the data messages are received by the at least one access point. A first value of range of the mobile unit from the access point is determined on the basis of time delay between the data message transmission and the acknowledgement signal. A second value of range is determined by measuring the signal strength of the acknowledgement signals received by the access point from the mobile unit corrected by a correction value. The first value of range is used to update the correction value.

In one arrangement the correction value is updated by determining the first value of range and the second value of range for a plurality of transmitted data messages and a plurality of received acknowledgement messages. A difference between the first value of range and the second value of range is determined for each of the plurality of data messages and plurality of received acknowledgement signals. The differences are averaged and the average of the differences is used to update the correction value. The plurality of data messages may be sent and the plurality of acknowledgement signals may be received by the same access point. Alternately, the plurality of data messages may be sent by more than one access point and the plurality of acknowledgement signals may be each received by an access point transmitting the corresponding message. The correction value may be updated by determining the first value of range and the second value of range for the transmitted data message and received acknowledgement message, determining a difference between the first value of range and the second value of range and updating the correction value using a selected fraction of the difference.

For a better understanding of the present invention, together with other and further objects thereof, reference is made to the following description, taken in conjunction with the accompanying drawings, and its scope will be pointed out in the appended claims.

DETAILED DESCRIPTION OF THE INVENTION

Figure 1:
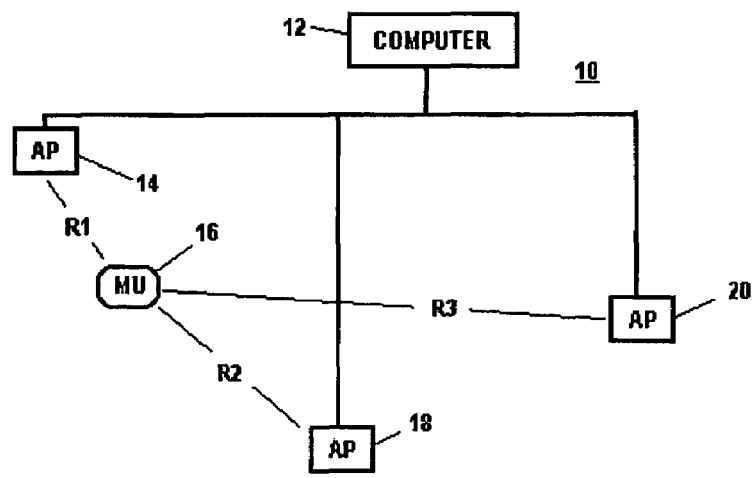
FIG. 1 is a simplified block diagram showing an exemplary system in which the method of the present invention may be practiced.

Referring to the simplified diagram of FIG. 1, there is schematically shown a wireless local area network system 10, which may for example follow the protocol of IEEE Standard 802.11. The system 10 of FIG. 1 includes a computer 12, which acts as a server, and is connected over a wired network to access points 14, 18 and 20 which are arranged at fixed locations within an area, such as a school, an industrial facility or a hospital. In addition to providing wireless communications between the server computer 12 and one or more mobile units 16 via an access point 14, 18, 20 with which the mobile unit 16 has become associated, the system 10 provides a function of locating the mobile units within the area.

In the system 10 location of a mobile unit is determined by receiving signals from the mobile unit at a plurality of access points and measuring the received signal strength, such as by the RSSI function of Standard 802.11 receivers. The system may be initially calibrated to form a database relating signal strength to location within the area, and the received signal strengths from a plurality, such as three or more access points 14, 18 and 20 are provided to server computer 12, which compares the signal strength to the database to derive a location within the area for mobile unit 16. Alternately the ranges R1, R2 and R3 between mobile unit 16 and access points 14, 18, 20 may be determined by a range equation form the received signal power level. The calibration of system 10 or the use of a range equation, assumes that all mobile units have identical transmitter power levels. The range equation assumes that range of a mobile unit can be determined by assuming that signal strength varies with the square of range.

Since power level of transmitters used in mobile units may be initially different and may vary as the unit or its battery ages, a correction value may be provided which is associated with each mobile unit that compensates for variations from nominal transmitter power for that mobile unit. The correction value may be applied to the received signal strength measurement or to the range determination as an addition, subtraction or multiplication factor according to the value to which the correction value is applied. For example, if the correction value is applied to a signal strength value in decibels, the correction would be a value in decibels added to or subtracted from the signal strength value.

It may, however, be inconvenient in some applications to make measurements to determine the correction value to be applied to a particular mobile unit, since mobile units may be added to the system after the initial calibration of the system. In addition the transmitter power of the mobile unit may change over time.

Figure 2:
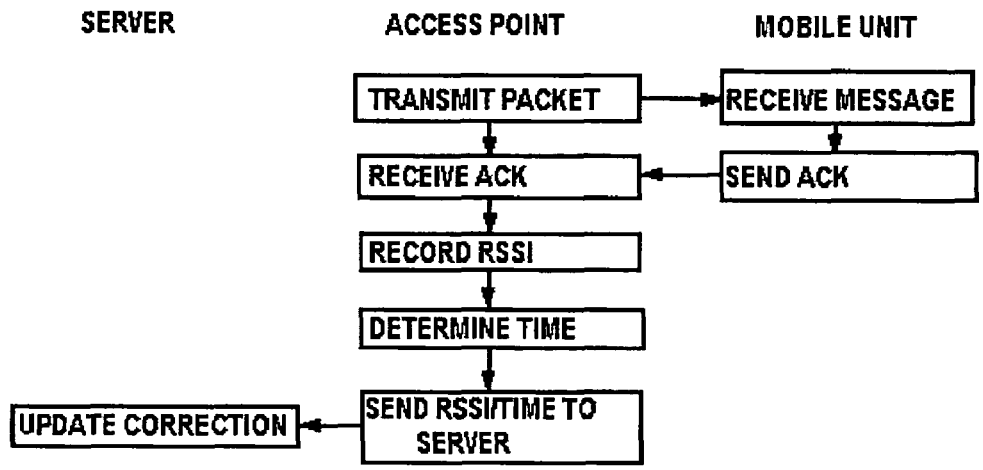
FIG. 2 is a flow diagram illustrating an embodiment of the method of the present invention.

Referring to FIG. 2 there is shown an embodiment of the method of the invention wherein correction values associated with a mobile unit are updated on a continuous or periodic basis in dependence on the current transmission characteristics of the mobile unit. According the method of the invention a first range between a mobile unit and one or more access points is determined using the round trip transmission time for signals between the access point and the mobile unit and a second range between the mobile unit and one or more access points is determined using received signal strength for transmissions from the mobile unit to the one or more access points applying the current correction value for the mobile unit. If the first range value and the second range value are the same, it is assumed the correction value is correct for that mobile unit. If the first range value and the second range value are different the correction value is updated using the measured range values assuming that the transmission time range value is correct.

Updating the correction value will depend in precise calculation upon the values to which the correction values are applied. If for example the correction value is signal strength in decibels, and the first range value indicates a range of 10 meters, and the second range value indicates a range of 20 meters, the correction value may require adjustment by 6 decibels, corresponding to a two-to-one range difference.

In accordance with the invention, it may be desirable to base updating of the correction value on more than a single measurement. Determining the value of range from a mobile unit to an access point can result in error from a variety of physical factors, such as mis-orientation for the respective antennas, intervening equipment, walls or people, or multi-path. Accordingly it may be desirable to make the measurements of range on a repeated basis and use average values to update the correction value. For example, in one arrangement of the method, the measurements may be repeated a number of times spaced over a period of time and the average values of range used to update the correction value. Determinations of range that indicate an excessive difference between the first and second range values may be discarded in computing the average. In another arrangement, a running correction may be used wherein the correction value is updated by only a selected value of the required update for each set of measurements, so that over a period of time the correction value approaches the determined correction value and errors are averaged out. In this approach measurements showing excessive differences between the range values may also be disregarded.

The frequency at which updating of the correction values is implemented depends on the particular system and its operational requirements. Generally re-calibration should not be so frequent that it adds significant burden to the overall traffic of the system. Changes to mobile unit transmitter power are not likely to be rapid or frequent. Further the operation can be spread over a time period since the correction values for all mobile units need not be updated at the same time. Accordingly mobile units may be updated on a cyclic schedule over a period of one month, for example.

While there have been described what are believed to be the preferred embodiments of the invention those skilled in the art will recognize that other and further changes and modifications may be made thereto without departing from the spirit of the invention and it is intended to claim all such changes and modifications as fall within the true scope of the invention.

We claim:

1. A method for calibrating an object location system which tracks transmitting mobile units by measuring received power level of signals transmitted by said mobile units and received by access points distributed over an area, comprising:

transmitting data messages from at least one of said access points to each mobile unit to be calibrated;

receiving acknowledgement signals from said mobile units corresponding to said data messages;

determining a first value for range of said mobile unit from said at least one access point on the basis of time delay between said data message and said acknowledgement signal;

determining a second value of said range of said mobile unit from said at least one access point by measuring signal strength of signals received by said access point from said mobile unit, corrected by a correction value corresponding to transmitter power of said mobile unit;

using said first value to update said correction value.

2. A method as specified in claim 1 wherein said updating of said correction value comprises determining said first value of range and said second value of range for a plurality of transmitted data messages and a plurality of received acknowledgement messages, determining a difference between said first value of range and said second value of range for each of said plurality of data messages and plurality of received acknowledgement messages, averaging said differences and using said average of said differences to update said correction value.

3. A method as specified in claim 2 wherein large values for said difference between said first value of range and said second value of range are discarded.

4. A method as specified in claim 2 wherein said plurality of data messages are sent by the same access point and wherein said plurality of acknowledgement signals are received by the same access point.

5. A method as specified in claim 2 wherein said plurality of data messages are sent by more than one access point and wherein said plurality of acknowledgement signals are each received by an access point transmitting the corresponding message.

6. A method as specified in claim 1 wherein said updating of said correction value comprises determining said first value of range and said second value of range for said transmitted data message and received acknowledgement message, determining a difference between said first value of range and said second value of range and correcting said correction value using a selected fraction of said difference.

* * * * *